(12) United States Patent
Yamakoshi et al.

(10) Patent No.: US 6,264,997 B1
(45) Date of Patent: Jul. 24, 2001

(54) ANTI-ARTERIOSCLEROTIC FOOD

(75) Inventors: Jun Yamakoshi; Makoto Saito; Akio Obata; Toru Izumi; Koichiro Tobe, all of Noda (JP)

(73) Assignee: Kikkoman Corporation, Chiba-Pref (JP)

( * ) Notice: Subject to any disclaimer, the term of this patent is extended or adjusted under 35 U.S.C. 154(b) by 0 days.

(21) Appl. No.: 09/577,359

(22) Filed: May 23, 2000

(30) Foreign Application Priority Data

May 24, 1999 (JP) .................................................. 11-142629

(51) Int. Cl.$^7$ .................................................. A61K 35/78
(52) U.S. Cl. .......................... 424/766; 424/725; 424/757; 426/655
(58) Field of Search ................................ 424/195.1, 725, 424/766, 757; 426/655

(56) References Cited

U.S. PATENT DOCUMENTS 4,232,122 * 11/1980 Zilliken .
5,904,924 * 5/1999 Gaynor .
5,997,935 * 12/1999 Diamond .

OTHER PUBLICATIONS

Yamakoshi, J. et al. Proanthocyanidin–rich extract from grape seeds attenuates the dvelopment of aoritc atherosclerosis in cholesterol– fed rabbiots, Atherosclerosis, p. 139–149 of vol. 142, 1999.*

E. A. Kirk et al., "Dietary Isoflavones Reduce Plasma Cholesterol and Atherosclerosis in C57BL/6 Mice but not LDL Receptor–Deficient Mice," 1998 American Society for Nutritional Sciences, pp. 954–959.

* cited by examiner

Primary Examiner—Francisco Prats
Assistant Examiner—K. C. Srivastava
(74) Attorney, Agent, or Firm—Young & Thompson

(57) ABSTRACT

A proanthocyanidin and an isoflavone are incorporated into a food. Compounding of grape seed extract as a proanthocyanidin and soy sauce cake extract as an isoflavone gives an anti-arteriosclerotic composition that is effective at a small intake.

3 Claims, No Drawings

ANTI-ARTERIOSCLEROTIC FOOD

BACKGROUND OF THE INVENTION

The present invention relates to an anti-arteriosclerotic food containing a proanthocyanidin and an isoflavone.

Cardiovascular diseases attributed to arteriosclerosis, such as ischemic cardiopathy and cerebral infarct, have given rise to a serious social problem on account of their high death rates in Europe and America. Japan has also been suffering a steep increase of cardiovascular diseases caused by arteriosclerosis with westernization of diet. For the time being, drug treatment of the arteriosclerotic cardiovascular diseases has a limit, and prevention by food-derived components, especially antioxidant substances is considered important. Various antioxidants of food origin, for example vitamin C and vitamin E have been studied to date from the standpoint of prevention of arteriosclerosis but have not yet attained sufficient prophylactic effects.

Prevention of arteriosclerosis by flavonoids has been attracting attention and been under study. In particular, proanthocyanidins were found to have an inhibitory effect on arteriosclerosis equally to probucol, an antihyperlipemic. However, since there is a limit of absorption of proanthocyanidins from the intestinal canal, the effects obtained from proanthocyanidins, even if ingested in a large quantity, are limited (see Jun Yamakoshi, et al., Atherosclerosis, vol. 142, pp. 139–149 (1999)). Isoflavones, on the other hand, exhibit dose-dependent effects when ingested alone but fail to produce a sufficient effect unless taken in a large amount.

SUMMARY OF THE INVENTION

An object of the present invention is to provide an anti-arteriosclerotic food which is more effective at a smaller amount than known anti-arteriosclerotic foods.

As a result of extensive studies, the present inventor has found that a combined se of a proanthocyanidin and an isoflavone as active ingredients produces synergism thereby to provide anti-arteriosclerotic foods which are more effective even when taken in a small amount and completed the present invention. The mechanism of the synergism is believed to reside in that oxidation of LDL (low density lipoprotein) which takes an important role in developing arteriosclerosis is suppressed by proanthocyanidin's capturing active oxygen species outside LDL and isoflavone's capturing active oxygen species inside and outside LDL.

DETAILED DESCRIPTION OF THE PREFERRED EMBODIMENTS

Proanthocyanidins are condensed tannin present in various plant parts, i.e., a group of condensation or polymerization compounds comprising, as a constituent unit, flavan-3-ol or flavane-3,4-diol. These compounds release anthocyanidins, such as cyanidin, delphinidin, and pelargonidin, upon being treated with an acid, on which the above naming is based. Proanthocyanidins include procyanidin, prodelphinidin, propelargonidin, and the like which may be oligomers made up of two, three or four units or polymers made up of ten or more units; and stereoisomers thereof. They are obtained by extracting various plant parts, such as grape seeds, cranberry fruit, apple fruit, adzuki beans (red beans), and bark of sugi trees (Japanese cedar), hinoki trees (Japanese cypress) or pine trees.

Products comprising proanthocyanidins as a main ingredient are available on the market, including Gravinol and KPA (both available from Kikkoman Corp.; prepared from grape seeds), Applephenon (available from The Nikka Whisky Distilling Co., Ltd.; prepared from immature apple fruit), and Pycnogenol (available from Horphag Research Ltd., Switzerland; prepared from bark of maritime pine trees).

The isoflavones which can be used in the present invention are obtained from various plant parts and roughly divided into glycosides and aglycons (non-sugar moieties of glycosides). Many of naturally-occurring isoflavones are glycosides. Isoflavone glycosides ingested into the body are decomposed by $\beta$-glycosidase to release aglycons, which are ready to be absorbed. Some persons are unable to take in aglycons because of lack of $\beta$-glycosidase. Therefore, isoflavone aglycons are superior to isoflavone glycosides in bioavailability.

Specific examples of isoflavones are daidzin, glycitin, genistin, daidzein, glycitein, genistein, 6"—O-acetyldaizin, 6"—O-malonyldaizin, 6"—O-acetylglycitin, 6"—O-malonylglycitin, 6"—O-acetylgenistin, and 6"—O-malonylgenistin. These isoflavones can be obtained by extracting various plant parts, such as leguminous plants (e.g., soybean and red clover (Trifolium pratense)), composite plants, and iridaceous plants. Isoflavones are also extractable from by-products obtained in the manufacture of tofu (soybean curd), miso (soybean paste), soy sauce, isolated soybean protein, and the like, such as liquid used for boiling soybeans and soybean whey. The extracted isoflavone glycosides may be treated with $\beta$-glycosidase or microorganisms having $\beta$-glycosidase to obtain the corresponding aglycons. Isofavones are also obtained by extracting soy sauce cake which is characterized by its high content of isoflavone aglycons.

Products comprising isoflavones as main ingredients are commercially available, including SoyAct (isoflavone aglycons prepared from fermented soybean extract; available from Kikkoman Corp.), Novasoy (isoflavone glycosides prepared from soybeans, available from ADM Comp.), and Promensil (isoflavone aglycons prepared from red clover, available from Novogen Inc.).

It is essential for the anti-arteriosclerotic food according to the present invention to contain both a proanthocyanidin and an isoflavone as active ingredients. If desired, these essential active ingredients can be mixed with appropriate auxiliary components such as vehicles and made into convenient forms such as powders, tablets and capsules ready to be taken as health foods, nutrient subsidiary foods, or specified heath foods. Further, the food of the present invention can be added to various beverages and foods to make healthy foods. The food of the present invention can further contain various food ingredients, food additives or drugs which are inhibitory on arteriosclerosis, such as vitamin C and vitamin E.

Effective intakes of the proanthocyanidin and the isoflavone (in terms of aglycon) of the anti-arteriosclerotic food are 10 mg or more, preferably 20 to 500 mg, and 5 mg or more, preferably 10 to 300 mg, respectively, per day for an adult weighing, for example, 60 kg.

The present invention will now be illustrated in greater detail by way of Test Example and Examples.

TEST EXAMPLE 1

(1) Diet Materials
  (a) Standard diet:
    normal diet supplied by Funabashi Nojo which contains no components of soybean origin.

(b) Cholesterol:

available from Wako Pure Chemical Industries, Ltd. (c) Proanthocyanidin:

Gravinol Super (grape seed extract; proanthocyanidin content: 87%; supplied by Kikkoman Corp.) (d) Isoflavone aglycon:

Soy sauce cake extract as isoflavone aglycons was prepared as follows. Soy sauce cake weighing 20 kg was extracted by circulation with 40 l of 90% ethanol, and the extract was concentrated under reduced pressure to obtain 6 l of an enriched extract. To the enriched extract was added about 1 l of a 4M aqueous sodium hydroxide to adjust to pH 10, and the mixture was allowed to stand overnight to separate into an oily layer and an aqueous alkali layer. The aqueous alkali layer separated was adjusted to pH 4 with concentrated hydrochloric acid to form a precipitate, which was collected by filtration, washed with water, and freeze-dried to obtain 100 g of a soy sauce cake extract powder (isoflavone aglycons). The powder contained 42.9% of isoflavones (comprising 21.1% of daidzein, 19.2% of genistein, and 2.6% of glycitein), 11.2% of saponin, 12.6% of sugar, 13.2% of protein, 2.9% of water, 2.0% of ash, 5.0% of lipid, and 0.1% of fiber.

(2) Preparation of Diet Samples

The above-described materials were mixed up in a usual manner in accordance with the formulation shown in Table 1 below to prepare diet samples.

TABLE 1

Compounding Ratio in Diet Sample

| Sample No. | Standard Test Group | Formulation (%) | | | |
|---|---|---|---|---|---|
| | | Choles-Diet | Seed terol | Grape Cake Extract | Soy Sauce Extract |
| 1 | standard diet group | 100.00 | | | |
| 2 | cholesterol-rich diet group | 99.00 | 1.00 | 0 | 0 |
| 3 | 1.00% isoflavone-containing diet group | 96.67 | 1.00 | 0 | 2.33 |
| 4 | 0.33% isoflavone-containing diet group | 98.22 | 1.00 | 0 | 0.78 |
| 5 | 0.87% proanthocyanidin-containing diet group | 98.00 | 1.00 | 1.00 | 0 |
| 6 | 0.087% preanthocyanidin-containing diet group | 98.90 | 1.00 | 0.10 | 0 |
| 7 | (0.087% proanthocyanidin + 0.33% isoflavone)-containing diet group | 98.12 | 1.00 | 0.10 | 0.78 |

(2) Efficacy Test: confirmation of prophylactic effect on arteriosclerosis

Five to seven male NZW rabbits per group, each weighing 2 to 2.5 kg, were fed on the diet of Table 1 for 8 weeks. The daily diet intake was restricted to 90 g/rabbit. The rabbits were put to death under Nembutal anesthesia. The aorta was excised, placed in formalin, and stained with Sudan IV. The area ratio of lesions diagnostic of arteriosclerosis to the total inner surface of the examined aorta was determined with an image analyzer SP500f supplied by Olympus Optical Co., Ltd. The results obtained are shown in Table 2 below.

As is seen from Table 2, when a proanthocyanidin and an isoflavone are given jointly, synergism in inhibiting arteriosclerosis is observed to such a high degree that would not be reached simply by increasing the dosage of each of them given alone.

TABLE 2

Synergism of Proanthocyanidin and Isoflavone in Inhibition of Arteriosclerosis

| Diet Sample No. | Area Ratio of Arteriosclerotic Lesions in Aortic Arch (%) | Inhibition on Arteriosclerosis (%) |
|---|---|---|
| 1 | 0 | — |
| 2 | 74.8 ± 21.4 | — |
| 3 | 37.9 ± 10.8** | 49.3 |
| 4 | 54.8 ± 14.0* | 26.7 |
| 5 | 52.4 ± 10.4* | 37.7 |
| 6 | 46.6 ± 16.2* | 30.0 |
| 7 | 11.7 ± 7.5** | 84.4 |

Note:
*$p < 0.05$;
**$p < 0.01$ (indicative of significant difference from the cholesterol-rich diet group)

EXAMPLE 1

Preparation of Health Food in Tablets

Grape seed extract (proanthocyanidin content: 87%) 10 g

Soy sauce cake extract powder (isoflavone aglycon content: 43%) 10 g

Vitamin E ($\alpha$-tocopherol content: 98%) 1 g

Lactose 70 g

Magnesium stearate 8 g

The above components were compounded and tabletted to produce a health food in tablets each weighing 300 mg. The resulting tablets contained 8.7 g of the proanthocyanidins and 4.3 g of the isoflavones (aglycons) per 100 g. The tablets were highly stable and excellent in preservability and portability.

EXAMPLE 2

Preparation of Health Food in Hard Capsules

Grape seed extract (proanthocyanidin content: 87%) 40 g

Soy sauce cake extract powder (isoflavone aglycon content: 43%) 20 g

Potato starch 5 g

Light silicic acid anhydride 4 g

Calcium stearate 1 g

Lactose 30 g

The above ingredients were mixed and formulated into capsules each weighing 300 mg. Each capsule contained 34.8 g of the proanthocyanidins and 8.6 g of the isoflavones (aglycons). The capsules were highly stable and excellent in preservability and portability.

EXAMPLE 3

Preparation of Health Food (beverage)

The following ingredients were dissolved in water to make 1000 g, and the solution was sterilized by heating at 98° C. for 3 minutes. After cooling, the solution was subjected to sterile filtration and put in glass bottles in 50 g portions.

Grape seed extract (proanthocyanidin content: 87%) 6.09 g

Soy sauce cake extract powder (isoflavone aglycon content: 43%) 8.14 g

Glucose 300.00 g

Citric acid 10.00 g

Water 675.77 g

The resulting beverage contained 0.70 g of the proanthocyanidins and 0.35 g of the isoflavones (aglycons) per 100 g.

EXAMPLE 4

Preparation of Healthy Beverage

Grape seed extract (proanthocyanidin content: 87%) 20 g

Soy sauce cake extract powder (isoflavone aglycon content: 43%) 10 g

Orange juice 970 g

The above ingredients were mixed uniformly in a mixer. The resulting beverage contained 0.74 g of the proanthocyanidins and 0.43 g of the isoflavones (aglycon) per 100 g. The beverage was so palatable that one could drink everyday.

EXAMPLE 5

Preparation of Healthy Candy

Sugar 450 g

Thick malt syrup 428 g

Water 50 g

Fruit juice 20 g

Thickener 20 g

Ascorbic acid 10 g

Grape seed extract (proanthocyanidin content: 87%) 100 g

Soy sauce cake extract powder (isoflavone aglycon content: 43%) 50 g

Flavor 1 g

β-Carotene 1 g

Candy a piece of which weighed 5 g was made from the above ingredients in a usual manner. The resulting candy contained 0.87 g of the proanthocyanidins and 0.43 g of the isoflavones (aglycon) per 100 g.

What is claimed is:

1. An anti-arteriosclerotic food containing 0.6% by weight or more of a proanthocyanidin and 0.3% by weight or more of an isoflavone aglycon.

2. An anti-arteriosclerotic food according to claim 1, wherein said proanthocyanidin is an extract of grape seeds, and said isoflavone aglycon is an extract of soy sauce cake.

3. A method of inhibiting arteriosclerosis comprising applying an anti-arteriosclerotic food containing 0.6% by weight or more of a proanthocyanidin and 0.3% by weight or more of an isoflavone aglycon to an adult in such a manner that intakes of the proanthocyanidin and the isoflavone aglycon of the anti-arteriosclerotic food are 20 to 500 mg, and 10 to 300 mg, respectively, per day.

\* \* \* \* \*